(12) United States Patent
Hooi

(10) Patent No.: US 9,387,133 B2
(45) Date of Patent: *Jul. 12, 2016

(54) SANITARY PRODUCT FOR A HUMAN VAGINA

(75) Inventor: Yu Sing Hooi, London (GB)

(73) Assignee: Calla Lily Personal Care Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/437,587

(22) Filed: Apr. 2, 2012

(65) Prior Publication Data

US 2012/0197230 A1 Aug. 2, 2012

Related U.S. Application Data

(63) Continuation of application No. 10/582,445, filed as application No. PCT/GB2004/005128 on Dec. 10, 2004, now Pat. No. 9,265,668.

(30) Foreign Application Priority Data

| Dec. 12, 2003 | (GB) | ................................. 0328810.7 |
| May 20, 2004 | (GB) | ................................. 0411222.3 |

(51) Int. Cl.
| *A61F 13/15* | (2006.01) |
| *A61F 13/20* | (2006.01) |
| *A61F 13/472* | (2006.01) |

(52) U.S. Cl.
CPC ........... *A61F 13/47227* (2013.01); *A61F 13/20* (2013.01); *A61F 13/202* (2013.01);
(Continued)

(58) Field of Classification Search
CPC ........... A61F 2013/4729; A61F 13/202; A61F 13/2071; A61F 13/2022

USPC .................... 604/385.17, 385.18, 904, 11–18
See application file for complete search history.

(56) References Cited

U.S. PATENT DOCUMENTS

| 2,092,346 A | 9/1937 | Arone |
| 2,138,626 A | 11/1938 | Copen |

(Continued)

FOREIGN PATENT DOCUMENTS

| DE | 29611480 | 9/1996 |
| DE | 29620118 | 3/1998 |

(Continued)

OTHER PUBLICATIONS

English translation of WO 94/22405, Aug. 2008.
(Continued)

*Primary Examiner* — Michele M Kidwell
(74) *Attorney, Agent, or Firm* — Knobbe, Martens, Olson & Bear, LLP

(57) ABSTRACT

A sanitary product for use by women for the absorption of menstrual fluid has a plug and a pad joined by a sheath. The plug is substantially cylindrical so that it fits comfortably in a vaginal cavity. The pad remains outside the vaginal cavity, but has an absorbent layer on an inward side proximal to the plug and a liquid impermeable layer on an outward side. The sheath includes a tube of absorbent material for drawing excess menstrual fluid from the plug to the pad and has a layer of liquid impermeable material on its inside surface. It extends from an outward end of the plug, proximal to the pad, both to and through the pad. In use, a wearer can insert a finger into the sheath from the outward side of the pad to assist with insertion of the plug into the vaginal cavity.

21 Claims, 4 Drawing Sheets

(52) U.S. Cl.
CPC ......... *A61F13/2022* (2013.01); *A61F 13/2071* (2013.01); *A61F 2013/4729* (2013.01); *Y10T 29/49826* (2015.01)

(56) References Cited

U.S. PATENT DOCUMENTS

| | | | |
|---|---|---|---|
| 2,331,355 A | 10/1943 | Strongson | |
| 2,670,736 A | 3/1954 | Dunkelberger | |
| 2,733,714 A | 2/1956 | Haas | |
| 3,037,506 A | 6/1962 | Penksa | |
| 3,058,469 A | 10/1962 | Crockford | |
| 3,420,234 A | 1/1969 | Phelps | |
| 3,674,029 A | 7/1972 | Bates et al. | |
| 3,690,321 A | 9/1972 | Hirschman | |
| 3,905,372 A | 9/1975 | Denkinger | |
| 3,946,737 A | 3/1976 | Kobler | |
| 4,627,848 A | 12/1986 | Lassen et al. | |
| 5,113,873 A | 5/1992 | Boarman | |
| 5,180,059 A | 1/1993 | Shimatani et al. | |
| 5,193,684 A | 3/1993 | McDonald | |
| 5,290,262 A * | 3/1994 | Vukos et al. | 604/385.17 |
| 5,361,779 A | 11/1994 | Wilson, III | |
| 5,383,868 A | 1/1995 | Hyun | |
| 5,389,181 A | 2/1995 | Vukos et al. | |
| 5,690,625 A | 11/1997 | Widlund | |
| 5,827,256 A | 10/1998 | Balzar | |
| 5,891,123 A | 4/1999 | Balzar | |
| 6,059,763 A | 5/2000 | Brown | |
| 6,348,047 B1 | 2/2002 | Harper | |
| 6,840,927 B2 | 1/2005 | Hasse | |
| 6,863,664 B2 | 3/2005 | Wada | |
| 6,939,333 B1 | 9/2005 | Franklin, Jr. | |
| 7,112,192 B2 | 9/2006 | Hasse | |
| 8,672,872 B2 * | 3/2014 | Hooi | 604/11 |
| 2004/0024376 A1 | 2/2004 | Ohba | |
| 2004/0147893 A1 | 7/2004 | Mizutani et al. | |
| 2004/0147897 A1 | 7/2004 | Mizutani et al. | |
| 2004/0225272 A1 | 11/2004 | Karapasha | |
| 2005/0055003 A1 | 3/2005 | Bittner | |
| 2008/0077105 A1 | 3/2008 | Hooi | |
| 2009/0131852 A1 | 5/2009 | Hooi | |

FOREIGN PATENT DOCUMENTS

| | | |
|---|---|---|
| EP | 0 104 039 A1 | 3/1984 |
| EP | 136524 A1 | 4/1985 |
| EP | 1 206 925 A2 | 5/2002 |
| FR | 2590161 | 11/1985 |
| FR | 2 653 328 | 10/1989 |
| JP | 08-112311 A | 5/1996 |
| JP | 2000-237234 | 9/2000 |
| JP | 2003-010243 | 1/2003 |
| JP | 2005-177074 A | 7/2005 |
| WO | WO 94/22405 | 10/1994 |
| WO | WO 02/058611 A1 | 8/2002 |
| WO | WO 03/015676 A2 | 2/2003 |

OTHER PUBLICATIONS

International Search Report and Written Opinion dated Jul. 25, 2006 for International Application No. PCT/GB2006/001802.
International Search Report and Written Opinion dated Apr. 11, 2005 for International Application No. PCT/GB2004/005128.

* cited by examiner

SANITARY PRODUCT FOR A HUMAN VAGINA

This application is a continuation application of U.S. patent application Ser. No. 10/582,445, filed Sep. 25, 2006, now U.S. Pat. No. 9,265,668 which claims the benefit of PCT/GB2004/005128, filed Dec. 10, 2004, which claims the benefit of Application No. GB 0328810.7, filed on Dec. 12, 2003 and Application No. GB 0411222.3, filed May 20, 2004. Each of the aforementioned applications is hereby incorporated herein by reference in its entirety.

FIELD OF THE INVENTION

This invention relates to a sanitary product. More specifically, the invention relates to a sanitary product for use by women for the absorption of menstrual fluid.

BACKGROUND OF THE INVENTION

During menstruation, women generally choose to use either a tampon or a sanitary towel to absorb menstrual fluid. Their choice is influenced by the distinct advantages and disadvantages of tampons and sanitary towels.

Unlike sanitary towels, tampons are inserted into the vaginal cavity. This means that they are not visible, even if the user is wearing tight fitting clothing. Women also tend to be less conscious that they are using a tampon than a sanitary towel. These advantages are decisive for many women.

However, tampons have their disadvantages. Perhaps most importantly, tampons that remain inserted for too long can cause toxic shock syndrome and in some cases death. Other medical issues include a recommendation that tampons are not used when an intrauterine device (IUD) has recently been inserted and evidence that tampon use can predispose women to endometriosis. Tampons also have a number of perceptual and practical disadvantages. Tampons can be difficult to insert. Women who are not sexually active may not therefore feel comfortable using a tampon. Indeed, in some cultures, insertion of a tampon into the vaginal cavity is objectionable. Finally, women with heavy menstrual flow can experience some leakage and have some abdominal discomfort with tampon use.

Sanitary towels avoid some of the disadvantages of tampons. They are worn such that they cover the opening of the vaginal cavity, i.e. externally. This means that all the medical disadvantages of tampons (toxic shock syndrome, problems with new IUDs and predisposition to endometriosis) are avoided. Any perceptual issues regarding insertion into the vaginal cavity are also avoided and sanitary towels can be more practical for women with heavy menstrual flow, as they are usually less likely to leak than tampons. Finally, sanitary towels find particular use after giving birth or after termination of a pregnancy.

Nonetheless, sanitary towels have their own disadvantages. Even the smallest and most discrete sanitary towel is visible to some extent. Sanitary towels generally need to be held in position, e.g. by adhesion to panties or by a belt. They are large in comparison to tampons, which makes them less convenient to carry around or to dispose of. Women also tend to be more aware that they are wearing a sanitary towel than a tampon, as sanitary towels are less comfortable. Finally, sanitary towels are a little less hygienic than tampons as they can cause some mixing of bodily fluids.

It can therefore be appreciated that neither tampons nor towels are ideal. However, the present intervention recognizes that a sanitary product combining some of the features of a tampon with some of the features of a towel can have many of the advantages, yet minimise the disadvantages, of both tampons and towels.

Combined tampons and towels have been suggested before. For example, patent publications U.S. Pat. No. 2,092,346, U.S. Pat. No. 2,331,355, U.S. Pat. No. 3,037,506, U.S. Pat. No. 3,420,234, U.S. Pat. No. 3,690,321, U.S. Pat. No. 6,059,763 and EP1206925 all describe sanitary products comprising combined internally worn plugs (e.g. "tampons") and externally worn pads (e.g. "sanitary towels") of various shapes and designs. However, all these sanitary products suffer from a number of disadvantages. In particular, they are difficult to fit.

A tampon is usually inserted using an introducer, which is a stiff tube of plastics or cardboard. The introducer is inserted into the vaginal cavity and the tampon is pushed through and out of the introducer into position. The introducer is then withdrawn from the vagina, leaving the tampon in place.

The sanitary products described in U.S. Pat. No. 2,092,346, U.S. Pat. No. 2,331,355, U.S. Pat. No. 3,037,506, U.S. Pat. No. 3,420,234, U.S. Pat. No. 3,690,321 and U.S. Pat. No. 6,059,763 each have an externally worn pad joined directly to an internally worn plug. An introducer cannot be used to insert the plugs of these products, as the introducer cannot be withdrawn over the pad. The plug must therefore be inserted manually, either by manipulating the pad or by manipulating the plug with the pad folded out of the way. This is awkward to say the least.

EP 1206925 suggests a slightly different approach in which a conventional tampon is removably attached to a pad using a string. This document suggests using an introducer to insert the tampon and attaching the pad after insertion. However, this is time consuming and fiddly.

The present invention seeks to overcome these problems.

SUMMARY OF THE INVENTION

According to the present invention, there is provided a sanitary product for insertion into a human vagina, the product comprising an internally wearable absorbent plug and an externally wearable absorbent pad joined to one another by a sheath that opens through the pad and is elastic in only a circumferential direction, which allows for radial expansion, such that a wearer's finger can be received in the sheath to assist insertion.

The invention can be thought of as a tampon attached to a sanitary towel by a tube. The tube passes through the sanitary towel to one end of the tampon. During insertion, a finger is inserted in the tube, i.e. through the pad, to the tampon such that the tampon can be easily manipulated.

In the context of this invention, internally wearable means inside the vaginal cavity. In other words, it means inwardly of the vaginal orifice. Externally wearable means outside the vaginal cavity. In other words, it means outwardly of the vaginal orifice. It is actually preferred that the pad of the invention is wearable in the vulva, e.g. between the labia majora.

The sheath is joined to an end of the plug that is nearest to the vaginal opening in use. It is also joined to the pad and opens through the pad so that a finger can be inserted into the sheath from the side of the pad that faces away from the body in use. This means that a wearer's finger can be inserted through the pad toward the end of the plug and movement of the inserted finger can easily manipulate the plug during insertion. Fitting the sanitary product of the invention is therefore far easier than fitting any previous combined sanitary product or, indeed, most tampons or sanitary towels. In particular, no separate introducer is needed and the product does not need to be held in place by adhesion to panties or by a belt.

In order to optimise the ease with which the plug can be manipulated by a finger, the sheath is typically flexible. This allows the wearer's finger to easily move the plug relative to the pad. It is also preferred that the sheath terminates at the plug. More specifically, the sheath may extend all the way to the end of the plug nearest the vaginal opening in use. This allows the finger to reach the plug and directly manipulate it.

Another advantage of the invention is that, although the wearer's finger may enter the vaginal cavity during fitting, the finger is inside the sheath and does not come into direct contact with the vagina. This makes fitting the sanitary product of the invention clean and hygienic. Furthermore, use of the product is more acceptable for sexually inexperienced women or those with cultural objections.

In this regard, it is preferred that the sheath is fluid impermeable in a direction from the outside of the sheath to the inside of the sheath, in other words, the sheath may comprise a liquid impermeable membrane. For example, the sheath may comprise a tube of liquid impermeable material. Bodily or other liquids will not therefore pass through to the inside of the sheath and the inserted finger is protected.

In order to further protect the inserted finger, the sheath may be closed where it joins the plug. In one example, the perimeter of a tube forming the sheath may be joined to the plug, but the inside of the tube may effectively be open to the plug. However, it is preferred that the liquid impermeable membrane or tube of liquid impermeable material is itself closed at the end of the sheath that joins to the plug. This ensures that any liquid absorbed by the plug does not pass into the inside of the sheath.

Whilst it is useful to protect the inserted finger with a liquid impermeable membrane, it is desirable for liquid to be able to pass from the plug to the pad. It is therefore preferred that the sheath can pass liquid along its length from the plug to the pad. In other words, the sheath may comprise a tube of absorbent material. This allows excess fluid absorbed by the plug to be passed to the pad. The absorptive capacity of the product is therefore maximised and the size of the plug and pad can be minimised.

In a particularly preferred example, the sheath comprises a tube of liquid impermeable material inside a tube of absorbent material. This allows liquid to pass from the plug to the pad, but not into the inside of the sheath.

Although, as described below, the plug has a diameter smaller than that of an average conventional tampon, in order to have sufficient absorbency the plug has a relatively wide diameter in comparison to an average vaginal orifice. It is therefore preferred that the sheath has a smaller diameter than that of the plug. As the sheath is positioned at the vaginal orifice in use, this reduces pressure exerted on the vaginal orifice by the product and significantly improves comfort for the wearer.

Nonetheless, the sheath should be able to receive a finger, which is likely to have roughly the same or a slightly larger diameter than a small conventional tampon. It is therefore particularly preferred that the sheath is resiliently expandable in a radial direction to receive a finger during insertion of the product into the vagina. For example, the sheath may be elastic in (only) a circumferential direction, which allows for radial expansion. (Significant elasticity in a longitudinal direction may be undesirable as it can lead to misplacement of the plug). More specifically, the absorbent and liquid impermeable tubes may be elastic in a circumferential direction.

Typically, the sheath extends for substantially 2.5 cm between an end of the plug and a surface of the pad closest to the plug. This length suitably positions the plug in the vaginal cavity.

Whilst only insertion of the sanitary product has been discussed above, it should be evident that removal of the product can easily be achieved simply by pulling the pad outward. This will draw the plug out of the vagina. However, the present invention recognizes that pulling the pad in this manner will almost inevitably cause the wearer to touch the side of the pad that is in contact with the vagina in use. This is undesirable, it is therefore preferred that the product further comprises a string attached to the plug to assist removal of the plug from the vagina. It is particularly preferred that the string extends along the inside of the sheath. The string can then extend through the pad and be accessible to a wearer at the opening of the sheath. When a wearer pulls on the string to remove the plug, there is no need to grasp the pad or plug, which improves hygiene.

The term string is not intended to be limiting to any particular type of twine or thread. Rather, it is a general term referring to any usable cord or tail which the wearer can pull to extract the plug.

Typically, the pad comprises an absorbent layer and a liquid impermeable backing sheet. Conveniently, the backing sheet may be integral with the liquid impermeable material of the sheath. This ensures that no liquid passes through the pad to the side of the pad that faces outwardly in use. Similarly, the absorbent layer of the pad may be integral with the absorbent material of the sheath.

The dimensions of the pad can be selected for best fit and to provide sufficient absorptive capacity. In particularly preferred examples, any or all of the following dimensions can be used: the pad may be substantially 6.5 cm long; the pad may be substantially 5.5 cm wide; and/or the pad may be substantially 0.5 cm thick.

It is also preferred that the pad is a flat ellipse with one end wider than the other. The pad folds along its major axis in use and the irregular elliptical shape allows it to conform to the typical female anatomy.

The plug is similar in construction to a conventional tampon. For example, it typically comprises a wad of absorbent material. In other words, it is generally solid. Indeed, it is typically a solid cylinder, e.g. of compressed cotton.

As mentioned above, excess liquid may pass along the sheath from the plug to the pad. The present invention recognizes that, even when a sheath of small diameter is provided for comfort, this passing of liquid from the plug to the pad allows the size of the plug to be minimised. Indeed, sufficient absorption capacity can be provided in a plug substantially smaller than an average conventional tampon. It is therefore preferred that the plug is 4 cm in length or less and 2 cm in diameter or less.

This small plug size significantly increases the comfort of the product without compromising absorptive capacity. Any of the other features of the invention can be incorporated in this sanitary product. In particular, the neck may be the sheath. The neck may at least have a smaller diameter than the plug for comfort.

In a particularly preferred embodiment, the plug is substantially 3.5 cm in length and 1.5 cm in diameter. Other than for women with large menstrual flow, these are the preferred maximum dimensions. Smaller dimensions may be suitable for women with light menstrual flow. It is therefore preferred that the plug is substantially 3.5 cm in length or less and 1.5 cm in diameter or less.

According to the present invention, there is also provided a method of manufacturing a sanitary product, the method comprising joining an internally wearable absorbent plug to an externally wearable absorbent pad by a sheath to produce the sanitary product described above.

Preferred embodiments of the present invention will now be described, by way of example only, with reference to the accompanying drawings.

DETAILED DESCRIPTION OF THE PREFERRED EMBODIMENTS

Figure 1:
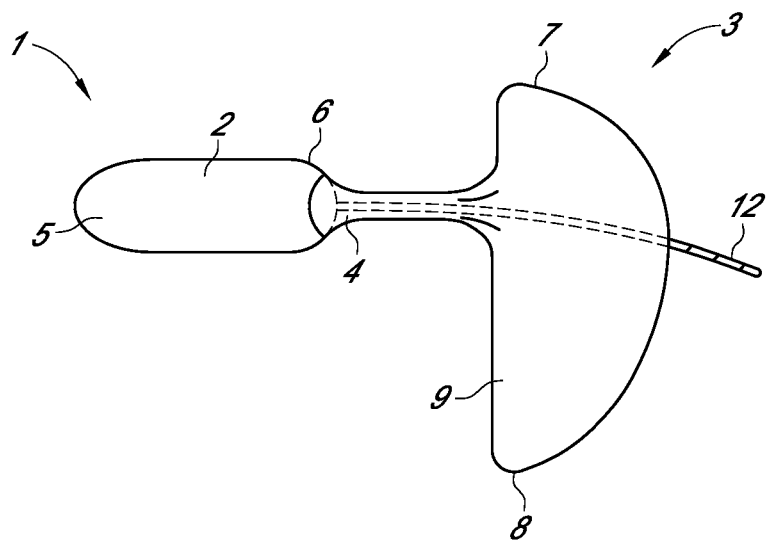
FIG. 1 is a side view of a sanitary product according to a preferred embodiment of the present invention.
Figure 2:
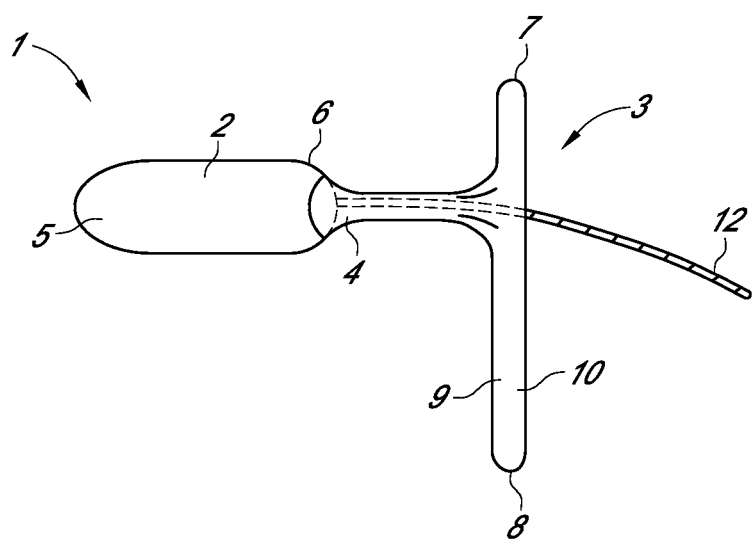
FIG. 2 is a side view of the sanitary product of FIG. 1 with an externally worn pad shown in an unfolded configuration.
Figure 3:
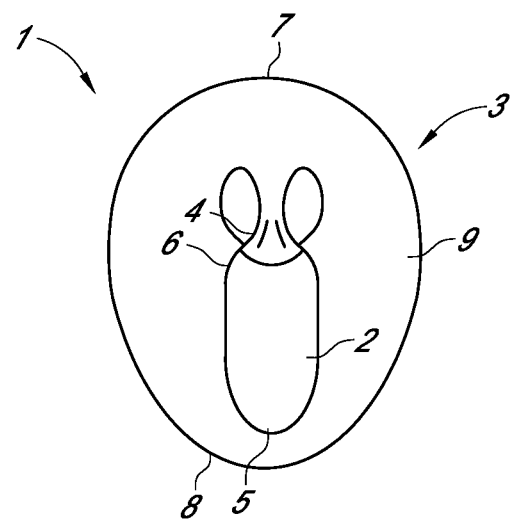
FIG. 3 is a front view of the sanitary product of FIG. 1.
Figure 4:
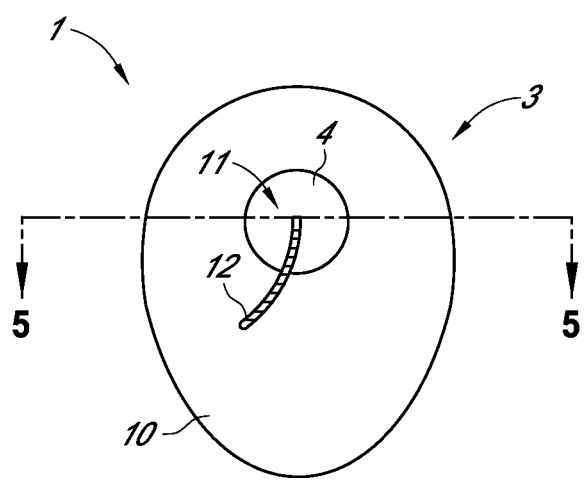
FIG. 4 is a rear view of the sanitary product of FIG. 1.
Figure 5:
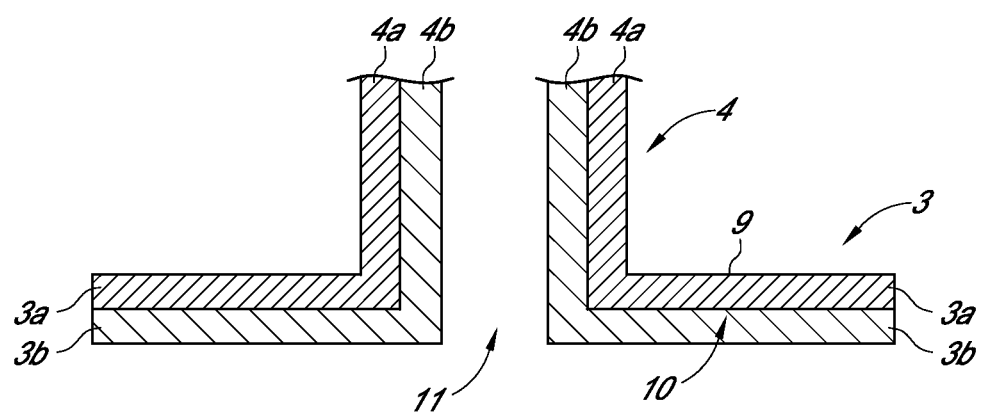
FIG. 5 is a schematic cross-sectional view through a portion of the pad and sheath of the sanitary product taken along line 5-5 of FIG. 4.
Figure 6:
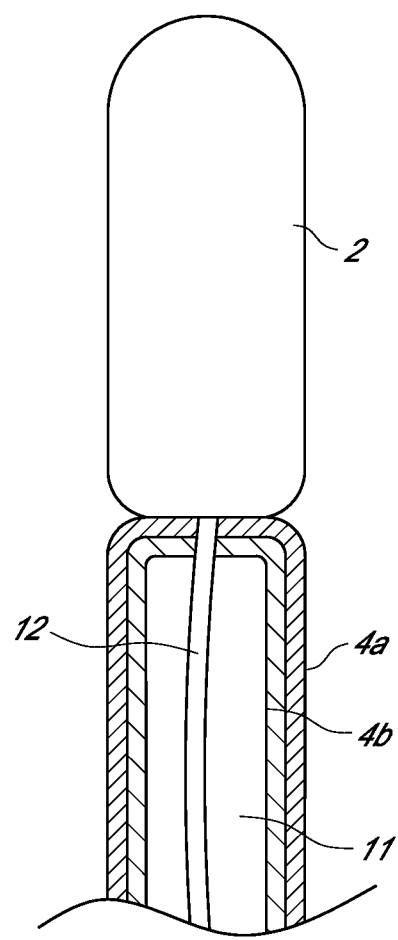
FIG. 6 is a schematic cross-sectional view through a portion of the plug and sheath of an embodiment of the sanitary product.

Referring to FIGS. 1 to 6, a sanitary product 1 according to a preferred embodiment of the present invention comprises a plug 2 and pad 3 joined by a sheath 4.

The plug 2 is substantially cylindrical so that it fits comfortably in a vaginal cavity. The end of the plug 2 that, in use, is inserted into the vaginal cavity first is referred to as the innermost end 5 of the plug 2. The end of the plug 2 that, in use, is inserted into the vaginal cavity last is referred to as the outermost end 6 of the plug 2. Both the innermost end 5 and outermost end 6 of the plug 2 are domed to ease insertion and removal of the plug 2 from the vaginal cavity. In another example, the outermost end 6 is flat.

The plug 2 is typically around 3.5 cm in length and around 1.5 cm in diameter. In other embodiments, these dimensions might vary within reasonable limits; say 4 cm or less in length and 2 cm or less in diameter. However, for women with light menstrual flow, an intact hymen or no sexual experience, the plug 2 is generally shorter and of smaller diameter.

In this embodiment, the plug 2 is made from compressed cotton. For example, a sheet of compressed cotton may be cut and rolled into an appropriate shape. Other suitable materials and constructions may be used as desired.

Typically, the pad 3 is substantially a flat egg-shape. In other words, the perimeter of the pad 3 is an ellipse having one end (broad end 7) broader or wider than the other end (narrow end 8). The side of the pad 3 in contact with the vagina in use is referred to as the inward side 9 (shown as the front of the sanitary product 1 in FIG. 3) and the side of the pad 3 in contact with clothing in use is referred to as the outward side 10 (shown as the rear of the product 1 in FIG. 4).

The pad 3 has an absorbent layer 3a on the inward side 9 and a liquid impermeable layer 3b on the outward side 10. In this embodiment, the absorbent layer 3a is made from compressed cotton and the liquid impermeable layer 3b is made from a polymeric material. Other suitable materials may be used as desired.

The pad 3 is typically 6.5 cm long and 5 cm wide at its largest dimensions. In other embodiments, these dimensions may vary within reasonable limits; say 6 cm to 7 cm in length and 4.5 cm to 5.5 cm in width. The absorbent layer 3a is typically 0.5 cm thick and, as the liquid impermeable layer 3b has negligible thickness, the pad 3 is also typically 0.5 cm thick overall. Again, in other embodiments, the thickness of the pad 3 might be between say 0.3 cm to 0.7 cm.

The sheath 4 is tubular and extends from the outward end 6 of the plug 2 to the pad 3. More specifically, the sheath 4 comprises a tube 4a of absorbent material with a layer of liquid impermeable material on its inside surface. In other words, there is a tube 4b of liquid impermeable material inside the tube 4a of absorbent material. The tube 4a of absorbent material extends to the inward surface 9 of the pad 3. Indeed, the absorbent material of the sheath 4 can be integral with the absorbent layer 3a of the pad 3. The tube 4b of liquid impermeable material extends through the pad 3 to the outward surface 10 of the pad 3. Indeed, the tube 4b of liquid impermeable material can be integral with the liquid impermeable backing of the pad 3.

The tube 4b of liquid impermeable material and hence the sheath 4 is open on the outward surface 10 of the pad 3. An opening 11 formed by the sheath 6 on the outward surface 10 of the pad 3 can be seen in FIG. 4. In this embodiment, the tube of liquid impermeable material is closed where it joins the plug 2. This prevents liquid absorbed by the plug 2 passing into the inside of the sheath 4.

The sheath 4 extends for around 2.5 cm from the outward end of the plug 2 to the inward surface of the pad 3, although in other embodiments this length may vary from say 2 cm to 3 cm. This length is enough to accommodate the tip of say an index finger to allow manipulation of the plug 2.

The diameter of the sheath 4 is smaller than that of the plug 2. More specifically, the external diameter of the sheath 4 at its smallest dimension might be 0.4 cm, although this might vary from say 0.2 cm to 0.8 cm in other embodiments. The small diameter is required to improve the comfort of the product 1 in the region of the vaginal orifice. However, this small diameter is clearly too small to allow a finger to be accommodated inside the sheath 4. The sheath 4 is therefore expandable in a radial direction. This is accomplished by the sheath 4 being elastic in the radial direction. In one embodiment, an elastic tube (not shown) is provided between the absorbent tube 4a and the liquid impermeable tube 4b of the sheath 4. In other embodiments, either or both of the absorbent and liquid impermeable tubes 4a, 4b of the sheath 4 are themselves elastic.

A string 12 is provided to aid removal of the product. In this embodiment, the string extends inside the sheath 4 from the outward end of the plug 2 and out through the opening 11. It is approximately 6 cm long.

In use, the sanitary product 1 is removed from its packaging and the pad 3 is gently folded along its major axis, i.e. a straight line extending between the broad end 7 and the narrow end 8 of the pad 3. One of the wearer's fingers is then inserted in the sheath 4 through the opening 11 to the outward end 6 of the plug 2. The elasticity of the sheath 4 allows it to expand radially and accommodate the finger.

The wearer orients the sanitary product 1 such the plug 2 extends longitudinally toward the vagina, the broad end 7 of the pad 3 is positioned approximately at the rear of the vagina, i.e. toward the anus, and the narrow end 8 of the pad 3 is positioned approximately at the front of the vagina, i.e. toward the pubic bone. The plug 2 can then be inserted through the vaginal orifice and into the vaginal cavity. The plug 2 is pushed into the vaginal cavity until the inward surface 9 of the pad 3 comes to rest against the surface of the vagina or, more specifically, the vulva, between the labia majora. The finger is then withdrawn from the sheath 4, leaving the sanitary product 1 in place.

During use, menstrual liquid is absorbed by the plug 2. Excess liquid is also drawn along the absorbent layer of the sheath 4 and absorbed by the pad 3. The product 1 has enough absorptive capacity to handle all but extremely excessive flows of menstrual fluid. However, the dimensions of the plug 2 mean that women have very little awareness of having the product 1 in place. The small diameter of the sheath 4 avoids any significant pressure being exerted on the vaginal orifice, which again improves comfort. Finally, the dimensions and shape of the pad 3 mean that it resides between the labia majora and is comfortable and unobtrusive.

When it is desired to remove the product 1, the wearer can grasp the string 12 and pull it to remove the plug 2 from the vagina. As the plug 2 is withdrawn, the outward surface 10 of the pad 3 can be grasped to fold the pad 3 around the plug 2 and sheath 4. Contact with menstrual liquid can therefore be avoided.

The described embodiments of the invention are only examples of how the invention may be implemented. Modifications, variations and changes to the described embodiments will occur to those having appropriate skills and knowledge. These modifications, variations and changes may be made without departure from the invention defined in the claims and its equivalents.

What is claimed is:

1. A sanitary product for a human vagina comprising an absorbent plug for absorption of menstrual fluid, an absorbent pad for absorption of menstrual fluid and a liquid impermeable flexible sheath disposed between the absorbent plug and the absorbent pad, the flexible sheath being a tube having an open proximal end and a closed distal end wherein the tube is itself closed at the end, the absorbent plug joined to the closed distal end of the tube entirely on the outside of the tube such that liquid cannot pass from the plug to the inside of the tube, and the absorbent pad joined to the proximal end of the tube,
    wherein said flexible sheath opens through the pad and is resiliently expandable in a radial direction such that a wearer's finger can be received in the sheath to assist insertion of the plug into a vaginal orifice, wherein the sheath is liquid impermeable in at least a direction from the outside of the sheath to the inside of the sheath.

2. The sanitary product of claim 1, wherein the pad comprises an absorbent layer on an inward side and a liquid impermeable backing sheet on an outward side.

3. The sanitary product of claim 1, wherein the pad comprises an absorbent layer on an inward side and a liquid impermeable backing sheet on an outward side and the backing sheet is integral with the liquid impermeable material of the sheath.

4. The sanitary product of claim 1, wherein the sheath passes liquid along the length of the sheath from the plug to the pad.

5. The sanitary product of claim 1, further comprising a tube of absorbent material outside the tube of liquid impermeable flexible sheath.

6. The sanitary product of claim 1, wherein the sheath has a smaller diameter than that of the plug when said sheath is unexpanded.

7. The sanitary product of claim 1, wherein the sheath extends for substantially 2.5 cm between an end of the plug and a surface of the pad closest to the plug.

8. The sanitary product of claim 1, further comprising a cord attached to the plug to assist removal of the plug from the vagina.

9. The sanitary product of claim 8, wherein the cord extends along the inside of the sheath.

10. The sanitary product of claim 1, wherein the plug is substantially not more than 4 cm in length and not more than 2 cm in diameter.

11. The sanitary product of claim 1, wherein the plug is substantially not more than 3.5 cm in length and not more than 1.5 cm in diameter.

12. The sanitary product of claim 1, wherein the plug is substantially 3.5 cm in length and 1.5 cm in diameter.

13. The sanitary product of claim 1, wherein the pad has the shape of a flat ellipse with one end wider than the other.

14. The sanitary product of claim 1, wherein the pad is substantially 6 to 7 cm long and 4.5 to 5.5 cm wide.

15. The sanitary product of claim 14, wherein the pad is substantially 6.5 cm long.

16. The sanitary product of claim 14, wherein the pad is substantially 5.5 cm wide.

17. The sanitary product of claim 1, wherein the pad is between 0.3 to 0.7 cm thick.

18. The sanitary product of claim 17, wherein the pad is substantially 0.5 cm thick.

19. A method of manufacturing a sanitary product, the method comprising joining an internally worn absorbent plug to an externally worn absorbent pad by a sheath to produce the sanitary product of claim 1.

20. A method of using a sanitary product according to claim 1 comprising inserting a finger into the sheath and pushing the plug into the vaginal orifice.

21. The sanitary product of claim 1, further comprising a cord attached to the plug to assist removal of the plug from the vagina wherein the cord extends along the inside of the sheath, wherein the sheath has a smaller diameter than that of the plug when said sheath is unexpanded, and wherein the pad comprises an absorbent layer on an inward side and a liquid impermeable backing sheet on an outward side.

* * * * *